(12) United States Patent
Guo

(10) Patent No.: US 6,753,449 B2
(45) Date of Patent: Jun. 22, 2004

(54) CLEAVABLE LINKER FOR SOLID PHASE SYNTHESIS

(75) Inventor: MaoJun Guo, Needham, MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 09/973,603

(22) Filed: Oct. 9, 2001

(65) Prior Publication Data

US 2003/0096301 A1 May 22, 2003

(51) Int. Cl.[7] .............................................. C07C 49/20
(52) U.S. Cl. ....................... 568/417; 560/205; 564/204; 558/251; 428/407; 435/6; 530/334
(58) Field of Search .................. 435/DIG. 42, DIG. 34, 435/6; 568/417; 560/205; 564/204; 558/251; 428/407; 530/334

(56) References Cited

U.S. PATENT DOCUMENTS

5,877,214 A    3/1999  Kim

FOREIGN PATENT DOCUMENTS

WO    WO 00/52018    9/2000

OTHER PUBLICATIONS

Moon, H.; Schore, N. E.; Kurth M. J. "A Polymer–Supported Chiral Auxiliary Applied to the Indollactonization Reaction: Preparation of g–Butyrolactones" J. Org. Chem. 1992, 57, 6088–6089.*

Zheng, A.; Shan, D.; Wang, B. "A Redox–Sensitive Resin Linker for the Solid Phase Synthesis of C–Terminal Modified Peptides" J. Org. Chem. 1999, 64, 156–161.*

Franzén, R. G., "Recent Advances in the Preparation of Heterocycles on Solid Support: A Review of the Literature," J. Comb. Chem., 2(3): 195–214 (2000).

Gordon, E. M., et al., "Applications of Combinatorial Technologies to Drug Discovery. 2. Combinatorial Organic Synthesis, Library Screening Strategies, and Future Directions," J. Med. Chem., 37(10): 1385–1401 (1994).

Guillier, F., et al., "Linkers and Cleavage Strategies in Solid–Phase Organic Synthesis and Combinatorial Chemistry," Chem. Rev., 100(6): 2091–2157 (2000).

Guo, M.J. et al., "Solid–Phase Stereoselective Synthesis of 2'–O–Methyloligoribonucleoside Phosphorothioates Using Nucleoside Bicyclic Oxazaphospholidines," Bioorg. Med. Chem. Lett., 8(18): 2539–2544 (1998).

Lorsbach, B.A., and Kurth, M. J., "Carbon—Carbon Bond Forming Solid–Phase Reactions," Chem. Rev., 99(6): 1549–1581 (1999).

Madsen, R., et al., "The Pent–4–enoyl Group: A Novel Amine–Protecting Group That Is Readily Cleaved under Mild Conditions," J. Org. Chem., 60: 7920–7926 (1995).

Sammelson, R. E. and Kurth, M. J., "Carbon—Carbon Bond–Forming Solid–Phase Reactions, Part II," Chem. Rev., 101(1): 137–202 (2001).

Seeberger, P. H. and Hasse, W.–C., "Solid–Phase Oligosaccharide Synthesis and Combinatorial Carbohydrate Libraries," Chem. Rev., 100(12): 4349–4393 (2000).

Yachi, K., et al., "Stereospecific Conversion of Iodohydrin Derivatives into Alkenes by Means of an Allylsilane–Titanium Tetrachloride System and its Application to Stereo–retentive Deoxygenation of Epoxides," Tet. Lett., 38(29): 5161–5164 (1997).

* cited by examiner

Primary Examiner—Bennett Celsa
Assistant Examiner—Jon D. Epperson

(57) ABSTRACT

Cleavable alkene-containing linkers and supports useful for the solid phase synthesis of chemical compounds, and combinatorial libraries of compounds, are disclosed. Also disclosed are methods of making and using the linkers and supports.

15 Claims, No Drawings

US 6,753,449 B2

CLEAVABLE LINKER FOR SOLID PHASE SYNTHESIS

BACKGROUND OF THE INVENTION

Combinatorial chemistry has recently emerged as an effective method for preparing large numbers of chemical compounds for use, e.g., in the discovery of biologically-active agents such as pharmaceutical drugs. In general, combinatorial chemistry is used to prepare collections of compounds, known as libraries, in which all the members of the library share a common core structural element. Such libraries can be prepared by a variety of methods, including solution-phase synthesis and solid-phase synthesis.

Solid-phase synthesis is usually performed by reaction of compounds which have each been immobilized by a covalent linkage to a solid or insoluble support material. The compounds are attached to the support material, which can be a polymeric resin such as polystyrene or polystyrene copolymer, through a linker, and when the synthesis of compounds is complete, the linker can be cleaved to release the final compound or compounds into solution.

The choice of linker for use in a synthesis depends upon the type of synthetic chemistry to be performed and on the conditions to be employed in the synthesis. In general, a linker is preferably inert to the reaction conditions employed during synthesis of the library, so as to avoid loss of compound by premature cleaving of the compound from the solid support. However, the linker should be selected to permit facile cleavage of the compounds from the solid support when the synthesis has been completed.

Numerous linkers have been proposed for use in solid phase combinatorial synthesis (for reviews, see, e.g., F. Guillier et al. *Chem. Rev.* (2000) 100(6): 2091–2158). Frequently, such linkers are cleavable under either acidic conditions or basic conditions. However, such linkers are not suitable for the preparation of compounds which are not stable to the acidic or basic conditions required for cleavage.

Other linkers have been developed which can be cleaved under more nearly neutral conditions. However, such linkers may be expensive to prepare and in some cases are not compatible with conditions which may be encountered during synthesis of a combinatorial library.

Accordingly, it would be desirable to provide new linkers which are easily and inexpensively prepared and which are compatible with a variety of reaction conditions.

SUMMARY OF THE INVENTION

The present invention relates to compositions and methods useful for performing solid-phase chemical synthesis reactions, including synthesis of combinatorial libraries of compounds. The compositions of the invention include linking moieties that can be cleaved under mild conditions, and are suitable for use with a variety of synthetic reaction conditions.

In one aspect, the invention provides a composition comprising an insoluble support covalently attached to a linker moiety. In this aspect, the linker moiety comprises a group represented by the formula (Formula I):

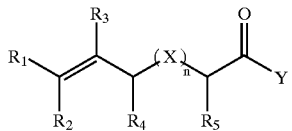

in which n is 0, 1 or 2; X is $CH_2$, O, S, or NR, in which R is alkyl (which may be substituted) or aryl (which may be substituted); Y is a leaving group, OR', NHR', or SR', in which R' is a positively-charged ion, optionally substituted alkyl or optionally substituted aryl; and $R_1$–$R_5$ are each independently selected from the group consisting of H, optionally substituted alkyl or optionally substituted aryl, nitro, alkoxy, aryloxy, cyano, azido, halogen, optionally substituted thioalkyl and optionally substituted thioaryl, and further wherein at least one of $R_1$–$R_5$ is covalently attached to an insoluble support. In certain preferred embodiments, n is 0. In other preferred embodiments, n is 1 and X is $CH_2$. In another preferred embodiment, Y is —OH. In certain embodiments, the insoluble support is agarose; in other embodiments, the insoluble support is polystyrene (including cross-linked polystyrene-divinylbenzene). In other embodiments, the insoluble support can be solubilized in a solvent. In certain preferred embodiments, $R_2$, $R_3$, and $R_4$ are H. In some preferred embodiments, $R_1$ is covalently attached to the insoluble suppor; in other preferred embodiment, $R_5$ is covalently attached to the insoluble support. In certain preferred embodiments, $R_5$ comprises an aminoalkyl group.

In another aspect, the invention provides a method of preparing a chemical compound on an insoluble support. In this aspect, the method comprises the steps of providing a composition of Formula I (in which n, X, Y, and $R_1$–$R_5$ as are defined above); covalently linking a first reactant to the linker moiety to provide a support-bound first reactant moiety; and reacting the support-bound first reactant moiety with a second reactant, under conditions such that a chemical compound on an insoluble support is prepared. In certain preferred embodiments of this method, n is 0. In other preferred embodiments, n is 1 and X is $CH_2$. In another preferred embodiment, Y is —OH, while in other preferred embodiments, Y is a leaving group. In certain embodiments, the insoluble support is agarose; in other embodiments, the insoluble support is polystyrene (including cross-linked polystyrene-divinylbenzene). In other embodiments, the insoluble support can be solubilized in a solvent. In certain preferred embodiments, $R_2$, $R_3$, and $R_4$ are H. In some preferred embodiments, $R_1$ is covalently attached to the insoluble suppor; in other preferred embodiment, $R_5$ is covalently attached to the insoluble support. In certain preferred embodiments, $R_1$ comprises an aminoalkyl group.

In another aspect, the invention provides a method of preparing a chemical compound. This method includes the steps of providing a composition of Formula I; covalently linking a first reactant to the linker moiety to provide a support-bound first reactant moiety; reacting the support-bound first reactant moiety with a second reactant, under conditions such that a chemical compound on an insoluble support is prepared; and cleaving the chemical compound from the insoluble support. In a preferred embodiment, the step of cleaving comprises contacting the chemical compound on an insoluble support with an electrophilic reagent under substantially neutral conditions. In a more preferred embodiment, the electrophilic reagent is $I_2$.

DETAILED DESCRIPTION OF THE INVENTION

Definitions

For convenience, certain terms used in the specification and claims are defined below.

The terms "insoluble support" or "solid support", as used herein, refer to a solid or insoluble support, commonly a polymeric support, to which a linker moiety can be covalently bonded by reaction with a functional group of the support. Many suitable supports are known, and include materials such as polystyrene resins, polystyrene/divinylbenzene copolymers, agarose, and other materials known to the skilled artisan. It will be understood that an insoluble support can be soluble under certain conditions and insoluble under other conditions; however, for purposes of this invention, a polymeric support is "insoluble" if the support is insoluble or can be made insoluble in a reaction solvent and under conditions used to effect the synthesis of chemical compounds on the support, or cleavage of compounds from the support, as described herein.

A variety of supports are known in the art and can be prepared by known techniques. For example, polymers including the carboxylic acid chloride functionality (e.g., —COCl) are known (see, e.g., P. Hodge and D.C. Sherrington, "Polymer-supported Reactions in Organic Synthesis", Chapter 1, (1980)) and can be prepared by treatment of conventional polymer-supported carboxylic acids (e.g., polyacrylic acids) with, e.g., thionyl chloride, oxalyl chloride, and the like. Polymeric supports including sulfonyl chloride functionalities can be obtained by the reaction of a polymer including sulfonic acid moieties with, e.g., thionyl chloride, or by other known methods, for example, the method described in U.S. Pat. No. 5,118,766. Benzyl halide-containing polymers are well known and include chloromethylated polystyrene (e.g., Merrifield resin). Such reactive supports can be reacted with a linker moiety (e.g., through reaction of an amino group of the linker moiety with a resin containing a carboxylic acid chloride) to form a resin-bound linker of the invention. Supports also include materials such as surfaces (e.g., glass or silicon surfaces), beads (such as glass or metallic beads), particles such as microspheres, carbon whiskers or rods, and the like.

In an alternative embodiment, the linker moiety can be attached to a soluble polymeric support such as a polyether moiety (see, e.g., U.S. Pat. No. 5,877,214 to Kim, and references cited therein). Soluble polyether supports have been used for organic synthesis methods in which reactions occur in the solution phase; the polymeric backbone, together with reactive groups, is dissolved in a solvent in which the polymer is soluble. At the conclusion of a given reaction step, a co-solvent (or non-solvent) is added to the reaction mixture, which causes the polymer to become insoluble and to separate from the liquid phase. The polymer, together with the pendant moieties which have been covalently modified, can then be isolated and washed, if desired, as in conventional solid-phase synthesis. Because such polymeric supports are generally handled (e.g., for purposes of purification) through insolubilization as described above, they will be considered to be "insoluble" supports for purposes of this invention.

The term "linker" as used herein, refers to a moiety capable of serving as an attachment point for a chemical compound or moiety (i.e., a desired product) that is prepared by solid-phase synthesis. The linker moiety should be capable of retaining the product to the solid support until cleavage of the product from the support is desired, yet permitting cleavage substantially without destruction of the product. Thus, a linker should preferably be substantially inert to reaction conditions used during the synthesis of the product, while being easily cleaved under conditions that do not destroy the product.

The term "cleave" or "cleaving", as used herein, refers to the separation of the product from the solid support. In general, a product is cleaved from a solid support when synthesis of the product is complete and the isolation or separation of the product from the solid support is desired. Conditions suitable for cleavage of products from the linkers of the invention are described in more detail, infra.

The term "alkyl", as used herein, includes cycloalkyl groups and refers to a straight, branched, or cyclic hydrocarbon radical having from 1 to 12 carbon atoms in the carbon chain (3 to 12 ring carbon atoms for cycloalkyl groups). Preferred alkyl groups are lower alkyl groups having 1 to 6 carbons in the carbon chain (3 to 6 ring carbons atoms for cycloalkyls). Alkyl groups also include groups in which the carbon chain is optionally partially unsaturated, as in alkenes and alkynes. Examples of alkyl groups include methyl, ethyl, butyl, isobutyl, sec-butyl, n-octyl, n-decyl, and the like; propenyl, 3-pentenyl, 2-butynyl, and the like. Alkyl groups can also be substituted at one or more positions on the carbon chain with groups such as halogen, hydroxy, amino (including mono- and disubstituted amino groups such as alkyl amino, dialkylamino, arylamino, and diarylamino), $C_1$ to $C_6$ acyloxy, $C_1$ to $C_6$ acyl, $C_1$ to $C_6$ alkoxy, aryloxy, thiol, $C_1$ to $C_6$ alkylthio, thioaryl, alkylcarbonyl, carboxyl, carboxamido, cyano, nitro, and sulfonyl (including alkylsulfonyl, aminosulfonyl and alkoxysulfonyl).

The term "aryl", as used herein, refers to monocyclic or bicyclic aromatic groups containing from 6 to 12 carbons in the ring portion, preferably 6–10 carbons in the ring portion, such as phenyl, naphthyl or tetrahydronaphthyl. The term "aryl" also includes heteroaryl groups; heteroaryl groups are groups having 5 to 14 ring atoms and 6, 10 or 14 pi electrons shared in a cyclic array; and containing carbon atoms and at least one (optionally two, three, four or five) oxygen, nitrogen or sulfur heteroatoms in the heteroaryl ring system. Examples of heteroaryl groups are: thienyl, benzo[b]thienyl, naphtho[2,3-b]thienyl, thianthrenyl, furyl, pyranyl, isobenzofuranyl, benzoxazolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolinyl, tetrahydroquinolinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl and phenoxazinyl groups and the like. Aryl groups can optionally be substituted on one to five positions on the aryl ring system with halogen, hydroxy, amino (including mono- and disubstituted amino groups such as alkyl amino, dialkylamino, arylamino, and diarylamino), $C_1$ to $C_6$ acyloxy, $C_1$ to $C_6$ acyl, $C_1$ to $C_6$ alkoxy, thiol, $C_1$ to $C_6$ alkylthio, thioaryl, alkylcarbonyl, carboxyl, carboxamido, cyano, nitro, and sulfonyl (including alkylsulfonyl, aminosulfonyl and alkoxysulfonyl).

The term "aralkyl" or "arylalkyl" as employed herein by itself or as part of another group refers to $C_{1-6}$ alkyl groups having an aryl substituent, such as benzyl, phenylethyl or 2-naphthylmethyl.

The term "cycloalkyl", as used herein, refers to cycloalkyl groups containing 3 to 9 carbon atoms, preferably 4 to 7 carbon atoms. Typical examples are cyclopropyl, cyclobutyl, cyclopentyl, cyclohexyl, cycloheptyl, cyclooctyl and cyclononyl.

The term "halogen" or "halo", as used herein, refers to chlorine, bromine, fluorine or iodine with chlorine being preferred.

The term "leaving group" as used herein, is art-recognized and refers to a functionality that upon heterolytic bond cleavage departs with an electron pair. In general, a leaving group will be a functionality that can be readily cleaved from a substrate moiety. One of ordinary skill in the art will be able to select a variety of suitable leaving groups. Examples of leaving groups (or, in some cases, the conjugate acid of a leaving group) include, e.g., carboxylates, halogens, tosylates, mesylates, certain alcohols (including phenols such as pentafluorophenol), N-hydroxysuccinimide (NHS), tetrazoles, triazoles, including 1-hydroxybenzotriazole (HOBT), imidazole, azide, ureas (as the tautomeric form, e.g., from the use of carbodiimide activating agents), cyanide and the like.

I. Linkers and Supports

In one aspect, the invention provides new linkers and insoluble supports for use in the synthesis of chemical compounds, e.g., for solid-phase synthesis of compounds, including combinatorial synthesis. The synthesized compound(s) are readily released from the linkers of the invention under near-neutral conditions, allowing the preparation of compounds which contain sensitive functional groups that might not survive cleavage conditions which require the use of acids or bases to liberate the desired compounds from the solid support.

In one embodiment, the invention provides a composition comprising an insoluble support covalently attached to a linker moiety, the linker moiety comprising a group represented by the formula (Formula I):

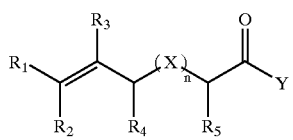

wherein n is 0, 1 or 2; X is $CH_2$, O, S, or NR, in which R is optionally substituted alkyl or optionally substituted aryl; Y is a leaving group, OR', NHR' or SR', in which R' is a positively-charged ion (including a proton, an ammonium ion, a metal ion (such as a sodium, potassium, lithium, or other metal ion)), optionally substituted alkyl or optionally substituted aryl; and $R_1$–$R_5$ are each independently selected from the group consisting of H, optionally substituted alkyl or optionally substituted aryl, nitro, alkoxy, aryloxy, cyano, azido, halogen, optionally substituted thioalkyl and optionally substituted thioaryl, and further wherein at least one of $R_1$–$R_5$ is covalently attached to an insoluble support. In a preferred embodiment, n is 0 or 1. In another preferred embodiment, $R_1$ is covalently attached to a solid support and $R_2$–$R_5$ are H.

As described above, the compositions of the invention comprise a support for synthesis covalently bonded to the linker moiety of FIG. 1; the support (which can be a resin (such as polystyrene), agarose, or other supports, e.g., as described herein) can be attached to the linker moiety through a chemical bond or through any moiety (such as a carbon or heterocycle-containing chain or even a cyclic moiety) capable of allowing the linker moiety to a) react with reagents for chemical synthesis and b) release a compound when chemical synthesis is complete. Examples of such attachment moieties are described herein, and can be, for example, $C_1$ to $C_6$ alkyl chain, which alkyl chain can be interrupted by one or two heteroatoms selected from S, O, N, P and Si. In certain preferred embodiments, the alkyl chain is interrupted by one N or O atom.

Certain preferred embodiments of the supports of the invention are described in more detail in the (non-limiting) Examples provided herein. For example, in an embodiment described in Examples 1 and 2, infra, the invention provides a support material of Formula I in which Y is —OLi (the lithium salt of the carboxylate), n is 0, $R_1$–$R_4$ are all hydrogen, and $R_5$ is a linking moiety of the structure —$(CH_2)_3$NH-SUP, in which SUP is a solid support (such as polystyrene resin or agarose beads). In the example of Example 3, infra, n is 0, Y is —OH (carboxylic acid), $R_2$, $R_4$ and $R_5$ are all hydrogen, $R_3$ is methyl, and $R_1$ is a bond to a solid support (in this Example, polystyrene resin). In Example 4, infra, n is 0, Y is —OH (carboxylic acid), $R_2$–$R_5$ are all hydrogen, and $R_1$ is a bond to a solid support (in this Example, polystyrene resin). In Example 5, infra, n is 0, Y is —OH (carboxylic acid), $R_1$–$R_4$ are all hydrogen, and $R_5$ is a bond to a solid support (in this Example, polystyrene resin). In Example 6, infra, n is 0, Y is —OH (carboxylic acid), $R_2$–$R_4$ are all hydrogen, $R_5$ is methyl, and $R_1$ is an N-atom-containing attachment to a solid support (in this Example, polystyrene resin). In Example 7, infra, n is 0, Y is —OH (carboxylic acid), $R_2$–$R_4$ are all hydrogen, $R_5$ is methyl, and $R_1$ is an O-containing attachment to a solid support (in this Example, polystyrene resin). In Example 8, infra, n is 1, X is —$CH_2$—, Y is —OH (carboxylic acid), $R_2$–$R_5$ are all hydrogen, and $R_1$ is a bond to a solid support (in this Example, polystyrene resin).

Compositions of Formula I can be prepared according to a variety of methods, including those described herein and other methods which are known to one of ordinary skill in the art. In general, the compositions can be prepared in at least two ways: (A) by preparing the linker moiety and attaching it to a suitable support; and (B) preparing a linker moiety that can be polymerized to form a linker-support composition of the invention.

In general, a linker moiety of the invention will include a carbonyl group spaced, by a distance of 2, 3 or 4 atoms (more preferably, 2 or 3 atoms), from a carbon—carbon double bond. This arrangement permits the cleavage (or release) of a product from the linker by treatment of the linker with an electrophilic reagent. Without wishing to be bound by any theory, it is believed that an oxygen atom of the carbonyl group can, through intramolecular attack upon the carbon—carbon double bond, form a 5-, 6-, or 7-membered ring (a lactone) with concomitant release of the product from the linker. Certain chemical protecting groups are known which are believed to be cleaved through this mechanism; see, e.g., Madsen, R. et al. *J. Org. Chem.* (1995) 60:7920; Guo, M J et al. *Bioorg. Med. Chem. Lett.* (1998) 8:2539–2544; and see generally Greene, T. W. and Wuts, P. "Protective Groups in Organic Synthesis" 3$^{rd}$ Ed. (1999), New York: John Wiley & Sons. Conditions suitable for cleavage of products from such linkers are described in more detail, infra.

A. Attachment of a Linker Moiety to a Support

A linker moiety of the invention can be prepared in a variety of ways. For example, in a preferred embodiment, a side-chain of the linker (e.g., $R_4$ or $R_5$ of Formula I) can be provided with a reactive group suitable for covalent attachment to a solid support. For example, as described in Examples 1 and 2 herein, an aminopropyl sidechain can be attached to a solid support by formation of an amide bond, e.g., by reaction of the nitrogen atom of the aminopropyl group with an activated carboxyl group of the solid support.

In another embodiment, a precursor of the linker moiety (e.g., a group which corresponds to $R_1$ of Formula I) can be provided with a reactive moiety such as an aldehyde or ketone group, which can be reacted with a solid-supported Wittig reagent to covalently link the linker to the solid support. For example, ethyl levulinate (which includes a ketone group) can be reacted with a resin-bound phosphonium salt to create a resin-bound linker (see Example 3, infra). Thus, a pre-formed linker moiety (or a precursor thereof) can be covalently secured to a solid support using a single-step reaction, which can, as described herein, serve both to tether the linker moiety to the support and to provide the olefinic bond necessary for linker cleavage by electrophilic activation. In an analogous fashion, a phosphonium salt can be reacted with a resin-bound aldehyde group to form a composition of the invention (see Example 4, infra).

Another method for attachment of the linker moiety to a solid support involves the use of radical reactions to form a covalent bond. For example, a linker moiety which contains a carbon—carbon double bond (such as a terminal alkenyl moiety or a styryl moiety) can be linked to a solid support, such as a resin, which also contains a carbon—carbon double bond, by using a radical initiator (such as 2,2'-azobisisobutyrylnitrile (AIBN)). Such a radical reaction will result in covalent attachment of the linker moiety to the support; the amount of linker attached to the support can be controlled by varying the number of reactive sites on the resin.

Another method for providing a linker covalently attached to a support is to copolymerize a monomeric precursor linker moiety (e.g., a free linker moiety which includes a terminal alkenyl or styryl group) with one or more monomeric blocks such as styrene or divinylbenzene, preferably under conditions known for the production of copolymer resins (such as free-radical polymerization). The copolymerization of the monomer units will result in incorporation of the linker moiety into the resin product, thereby providing the linker covalently linked to the support.

B. Attachment of Compounds to the Linker

Once the linker moiety is prepared and covalently bound to the support (e.g., a resin), the linker/support can be used for synthesis of organic compounds. In general, the synthesis will require the attachment of a reactive moiety to the linker, with subsequent modification of the reactive moiety to produce the desired product(s). Thus, for example, an amine-containing moiety can be coupled to the linker, e.g., through a carboxylate functionality on the linker, by well-known methods for forming an amide bond. For example, in the synthetic scheme shown for Example 9, below, piperazine is reacted with an activated carboxylic acid (as the NHS ester) to provide a piperazine-based scaffold for further synthetic manipulation. Many other compounds can be attached to the linker in a similar manner; for example, a molecule which contains a hydroxyl group can be esterified to the linker carboxylate, through an ester linkage, to provide a scaffold for synthesis of compounds; similarly, a thiol-containing compound can be attached to the linker (e.g., through a thioester group) to provide a template for synthesis. One of ordinary skill in the art will be aware of other methods for attaching compounds to the linker to provide a functionalized material useful for synthesis.

The functionalized support can then be used for solid-phase synthesis, e.g., according to methods well known to the ordinarily-skilled artisan; also see infra.

C. Detachment of Products from the Linker/Support

Once a desired compound (or compounds) has been prepared on the solid support/linker of the invention, the desired compounds can be released from the support, if desired, e.g., to provide compounds in solution for further purification or testing. It will be appreciated, however, that the compounds need not be released from the support, e.g., if it is desired to screen the compounds for a specific activity while the compounds are still attached to the linker/support.

To release the compounds, it is preferable to use relatively mild conditions, to avoid decomposition or undesired functionalization of the compounds. As described above, it is believed (without wishing to be bound by theory) that an oxygen atom of the carbonyl group of the linker portion can, through intramolecular attack upon the carbon—carbon double bond of the linker, form a 5- or 6-membered ring (or, in certain embodiments, a 7-membered ring) with concomitant release of the product from the linker upon hydrolysis. Thus, any reagent or condition that promotes such intramolecular attack can be employed to release compounds from the linker. Examples of reagents suitable for promoting cleavage are: iodine ($I_2$), bromine, iodine monochoride, N-bromosuccinimide, N-iodosuccinimide, mercuric chloride or other mercury(II) compounds, certain protic or Lewis acids, and the like. Such cleavage reactions will typically be performed by suspending the functionalized support, with the attached compound(s), in a suitable solvent with addition of the cleaving reagents. As noted above, a suitable nucleophilic reagent or solvent (such as water) should be added to facilitate the cleavage process.

Preferably, the release of compounds is performed under substantially neutral conditions (e.g., strong acids or bases are not used). In preferred embodiments, release of the compounds is performed at a pH in the range of 6.0–8.0, more preferably 6.5 to 7.5.

Once the compound has been released from the linker and solid support as described above, the desired compounds can be recovered by standard means. For example, when the cleavage reaction is performed on a suspension of resin in a solvent, the desired compounds will be released into, and preferably dissolved or suspended in, that solvent. Once the cleavage process is substantially complete, the resin can be separated from the liquid phase, e.g., by filtration, and the desired compound(s) can be recovered from the liquid phase by well-known techniques such as evaporation, crystallization, extraction, chromatography (including column chromatography, high-performance liquid chromatography (HPLC), and other chromatographic techniques), and other purification and isolation methods which will be apparent to one of ordinary skill in the art.

One advantage of the resin-bound linkers of the invention is that, in certain embodiments, the resin/linker can be regenerated and recycled after a synthesis is complete and the desired product has been released from the resin. Thus, for example, after a product has been released using iodine to promote intramolecular ring formation (i.e., the released resin will include a lactone ring) as described above, the spent resin (containing a vicinal acyloxyiodoalkyl functionality) can be recovered. The spent resin can be recycled for further use by, for example, treatment with allyltrimethylsilane and tin(IV) chloride or titanium(IV) chloride to ring-open and reduce the vicinal acyloxy-iodoalkyl functionality (see, e.g., Yachi, K. et al., *Tet. Lett.* 38(29):5161–5164 (1997)) to provide a carbon—carbon double bond. Alternatively, the lactone ring of the spent resin can be cleaved (e.g., by basic hydrolysis) to yield an iodohydrin (with a free carboxylate group also liberated). The iodohydrin can then be converted back to a double bond by reduction with a reagent such as zinc or magnesium metal. The resulting regenerated resin can then be used in a further synthesis by coupling reagents to the carboxylate group as described above.

II. Methods of Synthesis of Chemical Compounds

In general, the methods of the invention involve the attachment of chemical compounds or moieties to a solid-supported linker group as described above. Such chemical compounds or moieties can then be modified by stepwise reaction under a selected reaction scheme until a desired product is obtained. The desired compound can then be cleaved from the solid support under mild conditions which do not significantly destroy or modify the desired compound.

In one embodiment, the invention provides a method of preparing a chemical compound on an insoluble support. The method comprises the steps of providing a composition of Formula I; covalently linking a first reactant to the linker moiety to provide a support-bound first reactant moiety; and reacting the support-bound first reactant moiety with a second reactant, under conditions such that a chemical compound on an insoluble support is prepared.

In this embodiment, the first reactant is preferably an amine, an alcohol, or a thiol (or a conjugate base of any of these). For example, an amine can be attached to the linker moiety by formation of an amide bond with a carboxylate moiety of the linker (e.g., where Y is —OR' of Formula I), preferably through the use of an active ester or coupling reagent as is well known in the art. Similarly, an alcohol can be attached through an ester moiety by use of a suitably-functionalized linker (e.g., a linker of Formula I in which Y is a leaving group such as —Cl) or by use of a coupling agent (e.g., where Y of the linker of Formula I is —OR').

The step of reacting the support-bound first reactant moiety with a second reactant can include the use of a wide variety of synthetic reactions, such as those described herein or known to the ordinarily-skilled artisan.

The chemical compound can be screened for a desired activity by screening the compound on the bead according to methods known in the art (see, e.g., E. M. Gordon et al. *J. Med. Chem.* (1994) 37:1385–1401, and references cited therein). Alternatively, the chemical compounds, once prepared, can be cleaved from the support (e.g., as described herein) and screened in solution.

In another embodiment, the invention provides a method of preparing a chemical compound, the method including the steps of providing a composition of Formula I; covalently linking a first reactant to the linker moiety to provide a support-bound first reactant moiety; and reacting the support-bound first reactant moiety with a second reactant, under conditions such that a chemical compound on an insoluble support is prepared; and cleaving the chemical compound from the insoluble support.

The step of cleaving the chemical compound from the support can be performed as described previously. In certain embodiments, the step of cleaving comprises contacting the chemical compound on an insoluble support with an electrophilic reagent under substantially neutral conditions; in a preferred embodiment, the electrophilic reagent is $I_2$.

The reactions of the present invention may be performed under a wide range of conditions, though it will be understood that the solvents and temperature ranges recited herein are not limitative and only correspond to a preferred mode of the process of the invention.

A variety of synthetic methods are compatible with the compositions of the invention. For example, synthetic reactions, such as amidation, nucleophilic substitution, cycloadditions, aldol reactions, and the like, can be used to prepare a wide variety of compounds on the solid support (see, e.g., B. A. Lorsbach and M. J. Kurth, *Chemical Reviews* (1999) 99(6): 1549–1582; R. E. Sammelson and M. J. Kurth, *Chemical Reviews* (2001) 101(1): 137–202; P. H. Seeberger and W.-C. Haase *Chemical Reviews* (2000) 100 (12): 4349–4394; and R. G. Franzén *J. Comb. Chem.* (2000) 2(3): 195–214; and references cited therein). Deprotection steps can be performed if necessary; however, as with all synthetic reactions to be performed, it is preferred that deprotection steps are compatible with the linker moiety (i.e., such reaction steps do not destroy the linker, the solid support, or the compounds being synthesized on solid support). For example, a synthetic step which involves the use of $I_2$ could cause premature release of compounds from the solid support, which would likely result in lower yields of the desired product when synthesis is complete.

In general, it is desirable that reactions are run using mild conditions that will not adversely affect the substrate, the nucleophile, the intermediates, or the product. For example, the reaction temperature influences the speed of the reaction, as well as the stability of the reactants and catalyst. The reactions will usually be run at temperatures in the range of −78° C. to 100° C., more preferably in the range −20° C. to 50° C. and still more preferably in the range −20° C. to 25° C.

In general, the reactions according to the invention will be performed using a liquid phase, e.g., the reaction can take place on a support dissolved or suspended in a liquid phase. The reactions may be run in an inert solvent, preferably one in which at least one of the reaction ingredients (such as the support or, more preferably, at least one of the reagents) is substantially soluble. Suitable solvents include ethers such as diethyl ether, 1,2-dimethoxyethane, diglyme, t-butyl methyl ether, tetrahydrofuran (THF) and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide (DMF) and the like; or combinations of two or more solvents. In certain embodiments, the use of solvents such as water or alcohols (such as methanol, ethanol, propanol, t-butanol, and the like), either alone or in mixtures with other solvents, may be acceptable.

In certain embodiments it is preferable to perform the reactions under an inert atmosphere of a gas such as nitrogen or argon.

The invention also contemplates the synthesis of libraries or collections of chemical compounds. Combinatorial libraries of compounds can be prepared on solid supports by a variety of methods, some of which are known in the art (see, e.g., F. Guillier et al. *Chem. Rev.* (2000) 100(6): 2091–2158; E. M. Gordon et al. *J. Med. Chem.* (1994) 37:1385–1401). In general, preparation of a library involves the use of a plurality of supports (e.g., a plurality of resin beads, plastic "pins", resin crowns, a plurality of spatially-addressable points on a solid surface, etc.); by varying the reagents used to prepare chemical compounds on each of the plurality of supports, a variety of compounds can be prepared. For example, a plurality of supports (e.g., resin beads), each comprising a composition of Formula I, can be derivatized by linking a first reactant to the linker moiety of each support (e.g., resin bead) to provide a plurality of supports having a support-bound first reactant moiety; and each of the plurality of supports having a support-bound first reactant moiety can then be reacted with a second reactant, under conditions such that a chemical compound on an insoluble support is prepared on each support. The process can be continued, if desired, with third, fourth, etc. reactants to provide the desired chemical compounds. The first, second or subsequent reactants need not be the same for each support; generally, at least one of the reactants will differ between at least two supports, such that at least two different chemical compounds are prepared.

For example, in Example 9, infra, a plurality of supports (6) are reacted with piperidine and p-acetylbenzoic acid to provide a plurality of supports having a support-bound first reactant moiety; the derivatized supports are then divided into five separate portions and reacted with five different aldehydes to provide five different chalcone compounds on solid support. The five portions of support were then recombined and reacted with further reagents (an isatin and an amino acid) to produce five different spirocyclic compounds on the mixed resin supports. The compounds were then cleaved from the resin to provide a mixed library of compounds.

It will be appreciated, however, that in the above-described example, by varying the isatin reagent or the amino acid reagent, a combinatorial library of many members could be provided. For example, use of 5 aldehydes, 5 isatins, and 10 amino acids would provide a library having 250 compounds). Thus, the methods of the invention can be used to prepare libraries having at least 5, 10, 50, 100, 250, 500, 1000, 5000, or 10000 (or even more) compounds.

The following Examples are offered by way of illustration and not limitation.

III. EXAMPLES

Example 1

Synthesis of 2-allyl-5-aminopentanoic Acid

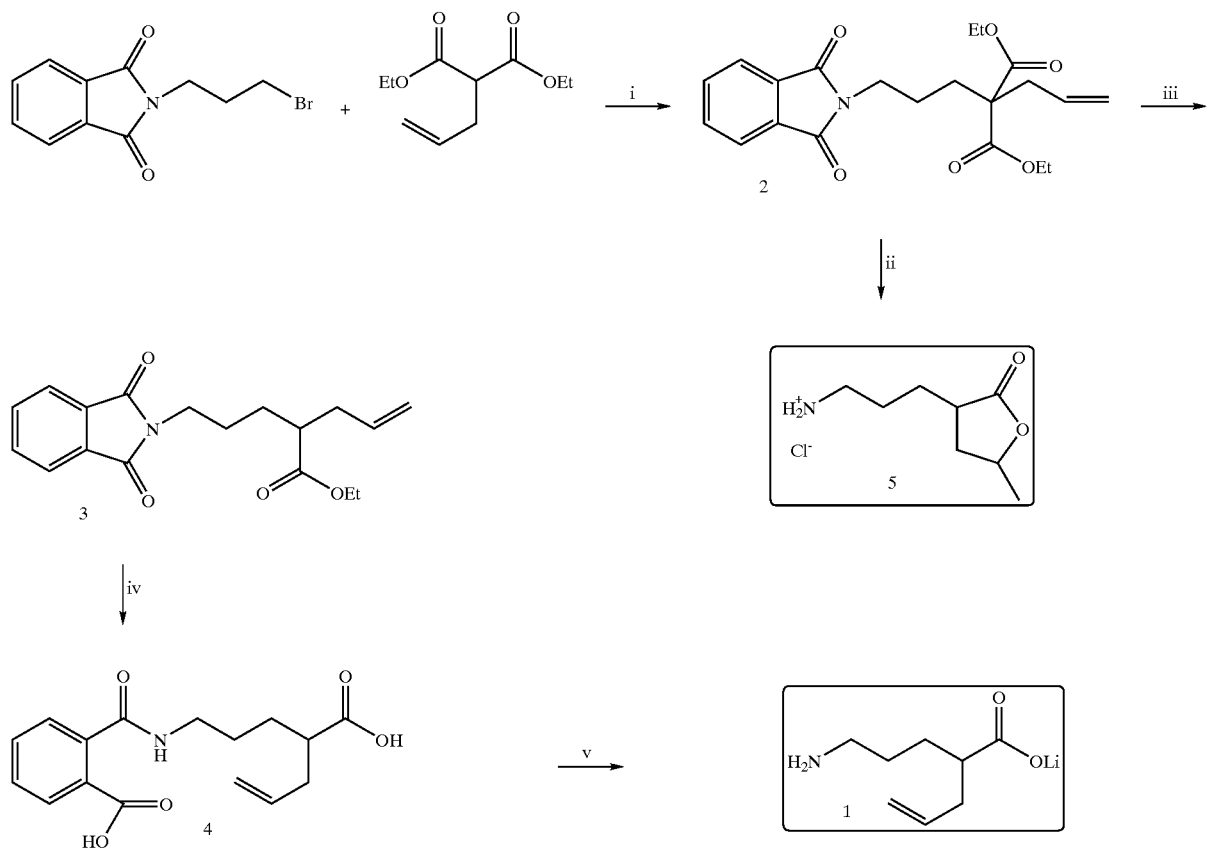

Diethyl allylmalonate was slowly added into a suspension of 1.1 eq. sodium hydride in DMF and stirred at RT for 5 minutes after addition. Then N-(3-bromopropyl)-phthalimide dissolved in DMF was added and the reaction mixture were stirred at 60° C. overnight. The solution was then slowly poured into 3 volumes of ice-water; alkylation product 2 precipitated, and the precipitate was collected by filtration. The filter cake was washed with water. HPLC analysis demonstrated that 2 was pure enough for use in the next step without further purification. Attempts to deprotect and decarboxylate 2 by refluxing in 6 M HCl did not yield the desired product. Instead, decarboxylation of 2 was achieved by refluxing in DMF with 1 eq of lithium bromide and 2 eq. of water for 40 hrs to yield desired intermediate 3. Compound 3 was converted into 4 by refluxing for 1 hr with 2 eq. NaOH (1M aq) in DMF, then 1 hr in water. After removing volatiles under vacuum, the residue was treated with 5 eq. of hydrazine, suspended in absolute ethanol, and refluxed overnight. Upon cooling, most of the liberated phthalhydrazide precipitated out; the precipitate was removed by filtration. After filtration, 2 eq. LiOH was added to the filtrate and the solvent was evaporated to afford crude 1 as its lithium salt. This was used directly for solid phase synthesis.

Example 2

Attachment of 2-allyl-5-aminopentanoic Acid to Insoluble Support

A. Attachment to Agarose

2-allyl-5-aminopentanoic acid (prepared in Example 1) was covalently attached to an agarose solid support by reaction with NHS Sephose 4 FF (Amersham Pharmacia Biotech; ligand density 20 micromoles/ml according to the manufacturer) in DMF at ambient temperature. After reaction was deemed complete, the agarose was filtered and washed with additional DMF and then the functionalized agarose support was stored in ethanol.

B. Attachment to Aminomethylpolystyrene

Aminomethylated polystyrene was purched from Nova Biochem (ligand density 1.1 mmol/g according to the manufacturer). The resin was reacted with succinic anhydride to generate carboxylate functional group on the resin. The carboxylate groups were activated with N-hydroxysuccinimide and DIC overnight prior to reaction with 2-allyl-5-aminopentanoic acid (prepared in Example 1) in DMF. After reaction was deemed complete, the resin was filtered and washed with additional DMF and dried to yield the functionalized resin support.

Example 3

Preparation of Linker on Resin Beads

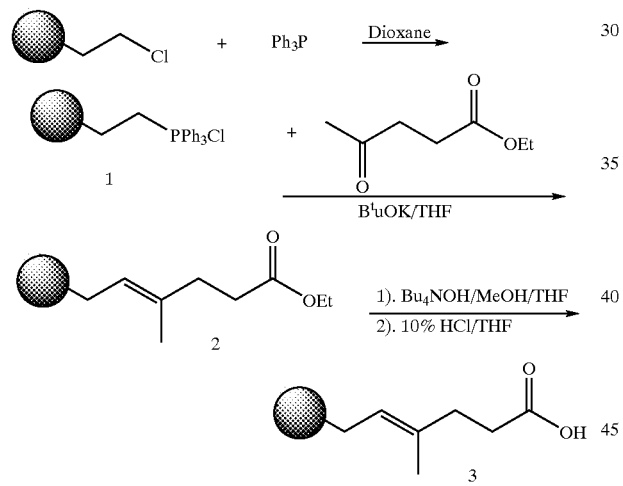

Preparation of PS—$CH_2P(Ph)_3{}^+Cl^-$ (1)

Chloromethylated polystyrene resin (from Nova Biochem) (32 g) containing 1.2 mmol of functional group/g was refluxed in 350 ml of dry dioxane containing 40 g of triphenylphosphine for 1 week. The resin particles were then collected on a glass filter, rinsed with THF (5×200 ml).

Preparation of PS—$CH\!\!=\!\!CMeCH_2CH_2COOEt$ (2)

The above resin (1) was suspended in 300 ml dry THF and cooled with an ice-bath. To the suspension, 46 ml of 1M potassium t-butoxide in THF was added; the resin became red. The suspension was stirred at room temperature for 1 hour, then cooled with an ice-bath. With stirring, 9 ml ethyl levulinate was added slowly. The ice-bath was removed and the mixture was refluxed overnight. The solvent was then drained and the resin resuspended in 300 ml THF containing an additional 9 ml ethyl levulinate and refluxed for another 24 hrs. The solvent was removed and the functionalized resin was washed with 2 portions (200 ml each) of THF, DMF, toluene and THF.

Preparation of PS—$CH\!\!=\!\!CMeCH_2CH_2COOH$ (3)

The above resin (2) was suspended in 550 ml THF, and 70 ml 40% $Bu_4NOH$ in methanol was added and the mixture was heated to reflux for 48 hours. The solvent was removed and the resin was washed with THF. The resin was then suspended in 300 ml THF containing 10% conc. HCl and stirred at room temperature for 1 hour. The solvent was removed and the resin was washed with THF and dried in vacuum at 50 C. for 15 hrs, yielding the functionalized resin 3.

Example 4

Preparation of Unsubstituted Linker on Resin Beads

Method 1

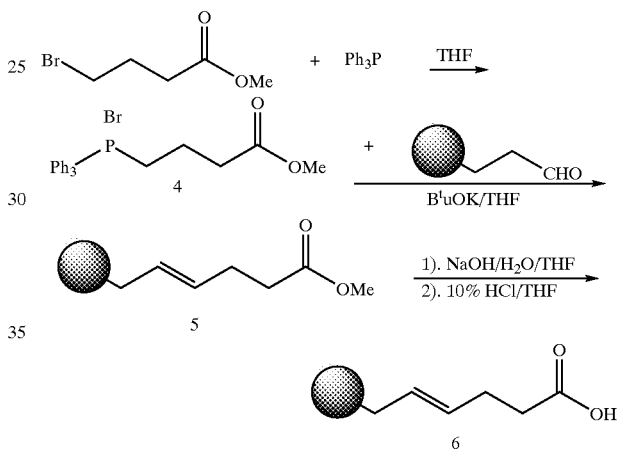

Preparation of $MeOOCCH_2CH_2CH_2P(Ph)_3{}^+Br^-$ (4)

Triphenyl phosphine (13.2 g, 50.2 mmol) was added to a solution of methyl 4-bromobutyrate (9.84 g, 52.7 mmol) in 200 ml dry THF and refluxed for 3 days. White solid precipitated from the solution; the reaction mixture was used in the next step without further purification.

Preparation of PS—$CH\!\!=\!\!CHCH_2CH_2COOMe$ (5)

Potassium t-butoxide (1M/THF, 50 ml, 50 mmol) was added to the preparation of $MeOOCCH2CH2CH_2P(Ph)_3{}^+Br$ (4) prepared in the above step and stirred at room temperature for 1 hr. No change in color was noted. PS-benzaldehyde (Argonaut Technologies, San Carlos, Calif., 1.29 mmol/g, 25 g, predried in vacuum at 50 C. for 15 hrs) was added, followed by 200 ml DMSO; the mixture was then heated at 100 C. overnight. HPLC analysis indicated the presence of released triphenylphosphine oxide. The solvent was removed, and the resin was washed with 2×200 ml each of MeOH, Water, MeOH and THF to afford the desired product.

Preparation of PS—$CH\!\!=\!\!CHCH_2CH_2COOH$ (6)

The above resin (5) was suspended in 500 ml THF, 50 ml 2M NaOH was added and the mixture was kept at refluxing for 24 hours. The solvents were removed and the resin was washed with THF. The resin was then suspended in 300 ml 10% conc. HCl in THF and stirred at room temperature for 1 hour. The solvent was removed by filtration and the resin was washed with THF and dried in vacuum at 50 C. for 15 hrs to yield functionalized resin 6.

with THF and dried in vacuum at 50 C. for 15 hrs to give the functionalized resin 6.

Example 5

Preparation of Allyl-functional Resin

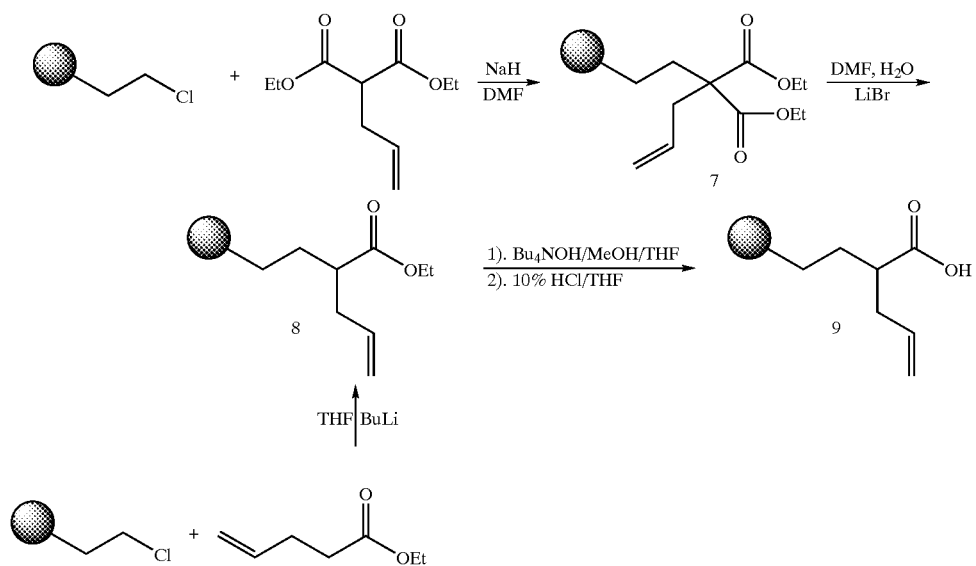

Method 2

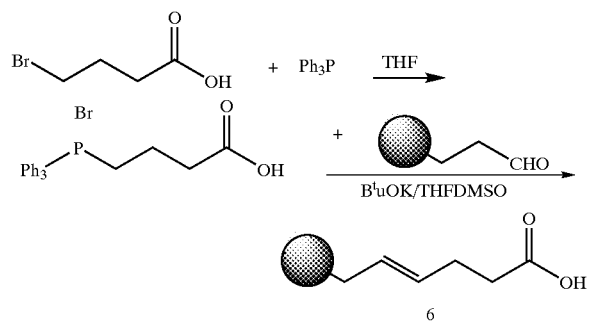

Triphenyl phosphine (26.5 g, 100.4 mmol) was added to a solution of 4-bromobutyric acid (13.5 g, 105.4 mmol) in 200 ml dry THF and refluxed for 3 days. The solvent was removed and the residue was dissolved in 400 ml DMSO. Potassium t-butoxide (1M/THF, 200 ml, 200 mmol) was added to the above solution of (3- carboxypropyl) triphenylphosphonium bromide (about 100 mmol based on complete conversion in the first step) and the mixture was stirred at room temperature for 1 hr. Polystyrene-benzaldehyde (from Argonaut Technologies, 1.29 mmol/g, 25 g, predried in vacuum at 50 C. for 15 hrs) was added, and the mixture was heated at 100 C. overnight. The solvents were removed and the resin was washed with 2×200 ml each of methanol, water, methanol and THF.

The above resin was suspended in 300 ml 10% conc. HCl in THF and stirred at room temperature for 1 hour. The solvent was removed by filtration and the resin was washed Preparation of PS-Diethyl allylmalonate (7)

Chloromethylated polystyrene resin (Nova Biochem) (2 g) containing 1.2 mmol of functional group/g was heated at 60 C. in 30 ml DMF containing 2.4 g of diethyl allylmalonate and 0.5 g sodium hydride (60% dispersion in mineral oil) for 18 hrs. The resin particles were then collected on a glass filter, rinsed with 2×200 ml each of methanol, water, and DMF to afford the functionalized resin (7).

Preparation of 2-PS-Ethyl pent-4-enoate (8)

Method 1.

The above resin 7 was suspended in 20 ml DMF containing 0.43 g lithium bromide (5 mmol, 2 eq.) and 0.18 ml water (4 eq.). The suspension was shaken at 140 C. for 50 hrs. The resin was then washed with 2×20 ml each of methanol, water, methanol and DMF.

Method 2.

Chloromethylated polystyrene resin (from Nova Biochem) (2 g) containing 1.2 mmol of functional group/g was shaken at room temperature in 30 ml dry THP containing 1.5 g of ethyl pent-4-enoate and 6 ml 2 M butyllithium in pentane for 18 hrs. The resin particles were then collected on a glass filter and rinsed with 2×20 ml each of MeOH, water and DMF.

Preparation of 2-PS-4-pentenoic acid (9)

The above resin (8, prepared by method 1) was suspended in 25 ml THF, 6.5 ml 40% Bu$_4$NOH in methanol was added, and the mixture was kept at refluxing for 48 hours. The liquid phased was removed and the solids were washed with THF. The resin was then suspended in 30 ml 10% conc. HCl in THF and stirred at room temperature for 1 hour. The liquid phase was separated and the solid was washed with THF and dried in vacuum at 50 C. for 15 hrs. This gives the functionalized resin 9.

Example 6

Preparation of Tertiary Amine-containing Resin

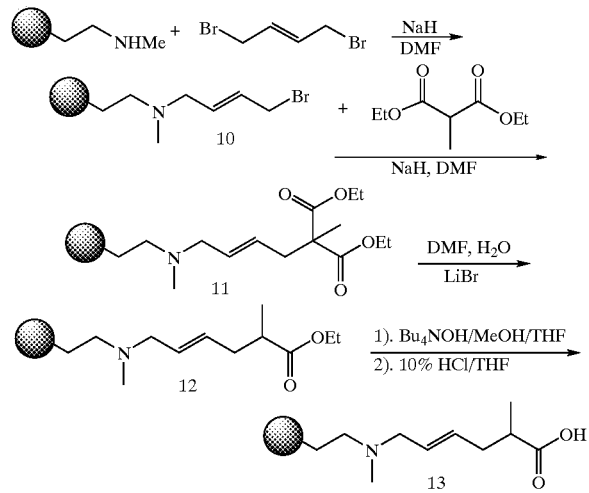

Preparation of 4-N-methyl-PS-1-bromo-2-butene (10)

N-Methylaminomethyl polystyrene resin (from Nova Biochem) (2 g) containing 1.13 mmol of functional group/g was heated at 60 C. in 30 ml DMF containing 2.5 g of 1,4-dibromobutene for 18 hrs. The resin particles were then collected on a glass filter and rinsed with 2×20 ml each of MeOH, water and DMF.

Preparation of 2-(4-N-methyl-PS-2-butene)-diethyl methylmalonate (11)

The above resin was heated at 60 C. in 30 ml DMF containing 2 ml diethyl methylmalonate and 0.5 g sodium hydride (60% dispersion in mineral oil) for 18 hrs. The resin particles were then collected on a glass filter, and rinsed with 2×20 ml each of MeOH, water and DMF.

Preparation of 6-N-methyl-PS-2-methyl ethyl hex-4-enoate (12)

The above resin (11) was suspended in 20 ml DMF containing 0.43 g lithium bromide (5 mmol, 2 eq.) and 0.18 ml water (4 eq.). The suspension was shaken at 140 C. for 50 hrs. The resin was separated and washed with 2×20 ml each of MeOH, water, MeOH and DMF.

Preparation of 6-N-methyl-PS-2-methyl 4-hexenoic acid (13)

The above resin (12) was suspended in 25 ml THF, 6.5 ml 40% Bu4NOH in methanol was added and the mixture was kept at refluxing for 48 hours. The liquid was removed and the resin was washed with THF. The resin was then suspended in 30 ml 10% conc. HCl in THF and stirred at room temperature for 1 hour. The resin was separated by filtration, washed with THF, and dried in vacuum at 50 C. for 15 hrs to give the functionalized resin 13.

Example 7

Preparation of Ether-containing Resin

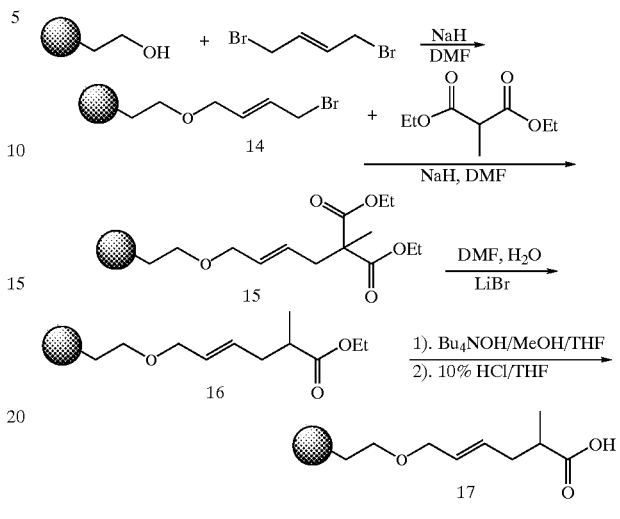

Preparation of 4-O-PS-1-bromo-2-butene (14)

Hydroxymethyl polystyrene resin (available from Nova Biochem) (2 g) containing 0.68 mmol of functional group/g was heated at 60 C. in 30 ml DMF containing 2.5 g of 1,4-dibromobutene and 0.5 g sodium hydride (60% dispersion in mineral oil) for 18 hrs. The resin particles were then collected on a glass filter, and rinsed with 2×20 ml each of MeOH, water and DMF.

Preparation of 2-(4-O-PS-2-butene)-diethyl methylmalonate (15)

The above resin (14) was heated at 60 C. in 30 ml DMF containing 2 ml diethyl methylmalonate and 0.5 g sodium hydride (60% dispersion in mineral oil) for 18 hrs. The resin particles were then collected on a glass filter and rinsed with 2×20 ml each of MeOH, water and DMF.

Preparation of 6-O-PS-2-methyl ethyl hex-4-enoate (16)

The above resin (15) was suspended in 20 ml DMF containing 0.43 g lithium bromide (5 mmol, 2 eq.) and 0.18 ml water (4 eq.). The suspension was shaken at 140 C. for 50 hrs. The resin was then separated and washed with 2×20 ml each of MeOH, water, MeOH and DMF.

Preparation of 6-O-PS-2-methyl 4-hexenoic acid (17)

The above resin (17) was suspended in 25 ml THF, 6.5 ml 40% Bu₄NOH in methanol was added and the mixture was kept at refluxing for 48 hours. The liquid was removed and the resin was washed with THF. The resin was then suspended in 30 ml 10% conc. HCl in THF and stirred at room temperature for 1 hour. The liquid was removed by filtration and the resin was washed with THF, and then dried in vacuum at 50 C. for 15 hrs. This gives the functionalized resin 17.

Example 8

Preparation of an Epsilon-unsaturated Resin

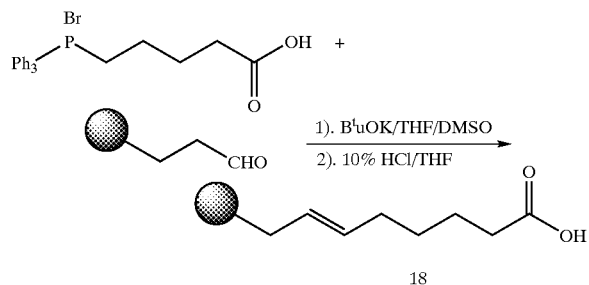

Preparation of PS—CH=CH CH$_2$CH$_2$CH$_2$COOH (18)

Potassium t-butyloxide (1M/THF, 100 ml, 100 mmol) was added to a solution of (4-carboxybutyl) triphenylphosphonium bromide (22 g, 50 mmol) in 400 ml DMSO, and the mixture was stirred at room temperature for 1 hr. PS-benzaldehyde (available from Argonaut Technologies, 1.29 mmol/g, 25 g, predried in vacuum at 50 C. for 15 hrs) was added, and the mixture was heated at 100 C. overnight. The resin was separated and washed with 2×200 ml each of MeOH, water, MeOH and THF.

The above resin was suspended in 300 ml 10% conc. HCl in THF and stirred at room temperature for 1 hour. The liquid was filtered off and the resin was washed with THF. Drying in vacuum at 50 C. for 15 hrs yielded the functionalized resin 18.

Example 9

Preparation of a Compound Library on Solid Support

A small compound library of five compounds was used to demonstrate the use of the compounds and supported linkers of the invention.

The library was prepared according to the scheme below:

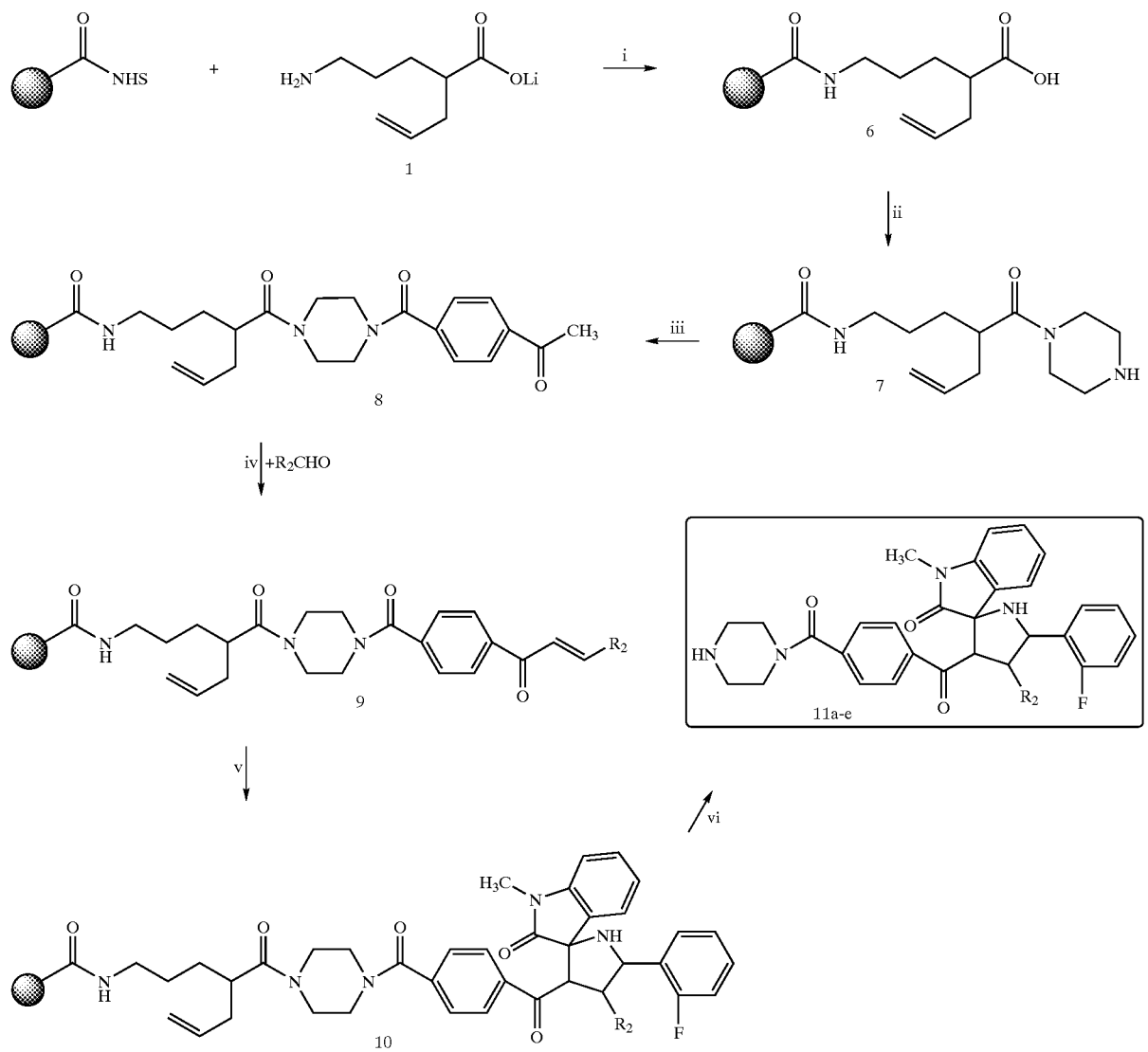

Conditions: i). 2 eq. of 1 (corresponding to the loadings on solid phase) in DMF, RT, 24 hrs. ii), 5 eq. N-hydroxysuccinimide (NHS) and diisopropylcarbodiimide (DIC) in DMF, RT 24 hrs, then 5 eq. piperazine RT 24 hrs. iii), 3 eq. HBTU, 3 eq. p-acetyl benzoic acid and 10 eq. N-methylmorpholine (NMM), DMF, RT 5 hrs. iv), 5 eq. aldehydes, 1 eq. sodium methoxide in EtOH, RT, 60 hrs. v), 5 eq. N-methyl isatin and (2-fluorophenyl) glycine, in dioxane/water (5/1), RT, 60 hrs. vi), 0.1M Iodine in THF /water (4/1), RT, 1 hr.

Thus, after covalent attachment of the linker moiety to the activated solid support (agarose or polystyrene) to form resin 6, standard amide bond formation (ii, iii; 6 to 8) was used to functionalize the resin. The functionalized resin 8 was divided into 5 portions and reacted with 5 different aldehydes (2-fluorobenzaldehyde, 3-formylbenzofuran, 2-phenoxybenzaldehyde, 2-(4'-chlorophenyl)thiobenzaldehyde and 5-(2'-chlorophenyl)-2-furaldehyde) to form chalcones 9. The resin portions were then pooled together and reacted with N-methyl isatin and (2-fluorophenyl) glycine to give spiro compounds 10. After cleavage with iodine/water/THF, compounds 11 were released and excess iodine was reduced with sodium sulfite. Analysis of the reaction mixture by HPLC showed 5 peaks for the five compounds in the mixture. LC-MS analysis gave the correct molecular weight for each compound.

Those skilled in the art will recognize, or be able to ascertain using no more than routine experimentation, numerous equivalents to the specific procedures described herein. Such equivalents are considered to be within the scope of this invention and are covered by the following claims.

The contents of all patents, patent applications, and publications described herein are hereby incorporated by reference in their entirety.

What is claimed is:

1. A composition comprising an insoluble support covalently attached to a linker moiety, the linker moiety comprising a group represented by the formula:

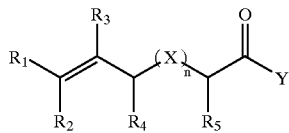

wherein
n is 0, 1 or 2;
X is $CH_2$, O, S, or NR, in which R is optionally substituted alkyl or optionally substituted aryl;
Y is a leaving group, OR', NHR', or SR', in which R' is a positively-charged ion, optionally substituted alkyl or optionally substituted aryl; and
$R_1$–$R_5$ are each independently selected from the group consisting of H, optionally substituted alkyl or optionally substituted aryl, nitro, alkoxy, aryloxy, cyano, azido, halogen, optionally substituted thioalkyl and optionally substituted thioaryl, and further wherein at least one of $R_1$–$R_5$ is covalently attached to the insoluble support.

2. The composition of claim 1, wherein n is 0.

3. The composition of claim 1, wherein n is 1 and X is $CH_2$.

4. The composition of claim 1, wherein Y is —OH.

5. The composition of claim 1, wherein the insoluble support is agarose.

6. The composition of claim 1, wherein the insoluble support is polystyrene.

7. The composition of claim 1, wherein the insoluble support can be solubilized in a solvent.

8. The composition of claim 1, wherein $R_2$, $R_3$, and $R_4$ are H.

9. The composition of claim 1, wherein $R_5$ is covalently attached to the insoluble support.

10. The composition of claim 1, wherein $R_1$ is covalently attached to the insoluble support.

11. The composition of claim 10, wherein $R_5$ comprises an aminoalkyl group.

12. A method of preparing a chemical compound on an insoluble support, the method comprising:
providing a composition of claim 1;
covalently linking a first reactant to the linker moiety to provide a support-bound first reactant moiety; and
reacting the support-bound first reactant moiety with a second reactant,
under conditions such that a chemical compound on an insoluble support is prepared.

13. A method of preparing a chemical compound, the method comprising:
providing a composition of claim 1;
covalently linking a first reactant to the linker moiety to provide a support-bound first reactant moiety; and
reacting the support-bound first reactant moiety with a second reactant,
under conditions such that a chemical compound on an insoluble support is prepared; and
cleaving the chemical compound from the insoluble support.

14. The method of claim 13, wherein the step of cleaving comprises contacting the chemical compound on an insoluble support with an electrophilic reagent under substantially neutral conditions.

15. The method of claim 14, wherein the electrophilic reagent is $I_2$.

* * * * *